(12) United States Patent
Clingan

(10) Patent No.: US 6,808,718 B1
(45) Date of Patent: Oct. 26, 2004

(54) METHOD OF TREATING FARROWING SOWS TO INCREASE PIG PRODUCTION

(75) Inventor: David L. Clingan, What Cheer, IA (US)

(73) Assignee: Elemental Technologies, What Cheer, IA (US)

( * ) Notice: Subject to any disclaimer, the term of this patent is extended or adjusted under 35 U.S.C. 154(b) by 110 days.

(21) Appl. No.: 10/235,867

(22) Filed: Sep. 5, 2002

(51) Int. Cl.[7] .......................... A61K 9/14; A61K 33/30; A61K 33/32
(52) U.S. Cl. .................. 424/423; 424/442; 424/489
(58) Field of Search ............................... 424/400, 422, 424/438, 442, 489

(56) References Cited

U.S. PATENT DOCUMENTS

| | | | | |
|---|---|---|---|---|
| 4,326,523 A | * | 4/1982 | Wolfrom et al. | ............ 424/426 |
| 5,066,498 A | | 11/1991 | McCauley, III | |
| 5,162,369 A | * | 11/1992 | Ashmead et al. | ........... 514/492 |
| 6,255,287 B1 | | 7/2001 | Watson et al. | |
| 6,387,419 B1 | * | 5/2002 | Christensen | .................... 426/2 |

* cited by examiner

*Primary Examiner*—James M. Spear

(57) ABSTRACT

The present invention provides a method of treating farrowing sows to increase pig production including the steps of determining the zinc concentration of swine blood or tissue samples, comparing the determined concentration with a predetermined adequate concentration range for swine, and then supplying chelated zinc to the sows when the determined concentration is below the adequate concentration range. The chelated zinc may be supplied to the sows through the water or feed, or even supplied by injection. The chelated zinc is preferably supplied during the lactation period since this is the time when the zinc is most critical in determining increased production in future litters and conception rates. Zinc in the chelated form is readily available to the sow and therefore rapidly corrects any deficiency that may exist. An alternate embodiment of this invention includes supplying chelated manganese in addition to the chelated zinc.

19 Claims, No Drawings

METHOD OF TREATING FARROWING SOWS TO INCREASE PIG PRODUCTION

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of swine production, and more particularly to a method of treating farrowing sows to increase pig production.

2. Description of Related Art

Large scale confinement production of domestic animals has led to highly sophisticated methods of producing animals under conditions where costs of production are closely scrutinized and controlled. In swine production a major factor lending to efficient production is the farrowing performance of the sows, and particularly the number of pigs per litter. Improvement in the litter size can have a major impact on the profitability of an operation.

Although numerous treatments and techniques have been utilized in the past, they are uniformly deficient with respect to their failure to provide a simple, efficient, and practical method of treating farrowing sows to increase pig production.

As a consequence of the foregoing situation, there has existed a longstanding need for a new and improved method of increasing pig litter size and the provision of such a method is a stated objective of the present invention.

BRIEF SUMMARY OF THE INVENTION

Briefly stated, the present invention provides a method of treating farrowing sows to increase pig production including the steps of determining the zinc concentration of swine blood or tissue samples, comparing the determined concentration with a predetermined adequate concentration range for swine, and then supplying chelated zinc to the sows when the determined concentration is below the adequate concentration range. The chelated zinc may be supplied to the sows through the water or feed, or even supplied by injection. The chelated zinc is preferably supplied during the lactation period since this is the time when the zinc is most critical in determining increased production in future litters and conception rates. Zinc in the chelated form is readily available to the sow and therefore rapidly corrects any deficiency that may exist. An alternate embodiment of this invention includes supplying chelated manganese in addition to the chelated zinc.

These and other attributes of the invention will become more clear upon a thorough study of the following description of the best mode for carrying out the invention.

DETAILED DESCRIPTION OF THE INVENTION

Zinc is an important micronutrient that functions to control the amount of water retention and it is necessary for longevity. High concentrations of zinc are found in the sex organs, liver, thyroid and milk. For swine, it is important to keep the zinc levels in balance. Zinc concentrations of 40–90 ppm in the tissue, and 0.70 to 1.50 ppm in the blood are generally regarded as acceptable and necessary for good health. An excess of zinc interferes with enzyme and lymph production and results in skin bleaching, ropy tails, and metallic element poisoning. A zinc deficiency interferes with utilization of copper and iron bringing about anemia, increases the need for vitamin A, and decreases growth and feed efficiency. Also, a deficiency results in skin disorders, skin lesions, eye disorders, white or cloudy eyes, and swelling of cells concentrated at the joints.

The present invention comprises a method of treating farrowing sows to increase pig production. The method involves determining the zinc concentration of blood or tissue samples, and supplying zinc in a chelated form to adjust for any deficiency to raise the zinc concentration to be within the acceptable and adequate range to increase the size of future litters and increase conception rates. The chelated zinc may be supplied in the water or feed, or supplied by injections, alone or in combination with other micronutrients such as manganese, magnesium, selenium, copper, iodine and iron. The zinc is preferably supplied by metering through a medicator into the water supply of the lactating sows. It is preferred to supply the chelated zinc during the lactation period since this is the time zinc is most critical in determining increased production in future litters and conception rates. Zinc is supplied in the chelated form since it is readily available to the sow to rapidly overcome any deficiency.

EXAMPLE 1

In a large scale confinement swine production setting, historical data covering farrowing performance indicated that the average total pigs per litter was 11.1. Using the method of the present invention, treatment was started and continued for 11 weeks. During the 11 week treatment period, the average total pigs per litter was 12.2. This represents a dramatic 10% increase in pig production which translates into significantly lower production costs.

The chelated zinc was supplied to batches of 24 farrowing sows over the 16–21 day lactation period. Each batch of 24 sows received three cups of 5% zinc in chelated form metered through a medicator into the water supply. The zinc level of the farrowing sows was determined by blood samples from the sows and tissue samples of their offspring. When the zinc level was determined to be below or at the lower end of the predetermined adequate concentration range, chelated zinc was supplied in the water.

The first step in the process is to take a baseline blood test to determine the level of zinc in the animals. It is not necessary to test all the animals. Instead, a one percent representative sampling is sufficient. The ideal range of zinc is 0.7 to 1.5 ppm. If the results of the test show a zinc level of less than 0.7 ppm, 1 ounce of chelated zinc is given to the animal. A second blood test is taken 4 weeks later. If the results of this second blood test remain less than 1.0 ppm, an additional ½ ounce of chelated zinc is provided. Once the zinc level is within the desired range, blood testing is done every three months to monitor the zinc level. If the test shows a zinc level of less than 1.0 ppm, additional administrations of chelated zinc in the amount of ½ ounce per administration are performed. If the results show a zinc level of greater than 1.5 ppm, no additional zinc is administered. Instead, blood testing is done on a per parity basis to determine when the zinc level has returned to the optimum range.

Manganese is another important micronutrient that is necessary for hormone, lymph and enzyme production as well as the normal function of the reproductive system. Balanced levels of manganese is important in swine with manganese concentrations of 2.3 to 4.0 ppm in the tissue generally acceptable and necessary for good health. An excess of manganese destroys enzymes and amino acid production, and decreases phosphorus utilization. A deficiency of manganese, which may result from an excess of calcium, phosphorus and iron, decreases the formation of fatty acids. Also, manganese deficiencies may cause bone deformities, degeneration of testicles, delayed or no heat period, tendency of offspring to abort or reabsorb at any stage, and lack of maternal instinct in the female.

EXAMPLE 2

Zinc and manganese were provided to the sows at the rate of 1 ounce of chelated zinc and 1 ounce of chelated manganese per sow. Zinc was supplied as indicated in Example 1, and manganese was supplied when the manganese level was determined to be below or at the lower end of the predetermined adequate manganese range from tissue samples from sows or their offspring.

This treatment with zinc and manganese caused the number of regular returns to be cut in half, as well as a reduction in regular return to estrous sows. Non-productive sow days, costing about two dollars each, were reduced by ten days thus reducing costs by twenty dollars per sow. Also, when zinc and manganese are brought to their proper levels, they have a balancing effect on other micronutrients such as copper, iron, phosphorus and molybdenum. Other results of this treatment include increased litter size; strong, heavier pigs; and a drastically reduced number of anemic offspring.

The chelated zinc and chelated manganese used in Examples 1 and 2 was supplied by Traylor Chemical & Supply Co., Inc. of Orlando, Fla.

The first step in the process is to take baseline blood and tissue tests to determine the level of the zinc and manganese in the animals. It is not necessary to test all the animals. Instead, a one percent representative sampling is sufficient. The ideal range of zinc in the blood is 0.7 to 1.5 ppm. The ideal range of manganese in the tissue is 2.3 to 4 ppm. If the results of the test show a zinc level of less than 0.7, 1 ounce of chelated zinc is given to the animal. If the results show a manganese level of less than 2.3, 1 ounce of chelated manganese is administered. A second blood and tissue test is taken 3 months later. If the results of this second blood test show a zinc level of less than 1.0 ppm, an additional ½ ounce of chelated zinc is provided. If the results of the second tissue test show a manganese level less than 3.0 ppm, an additional ½ ounce of chelated manganese is provided. Once the zinc and manganese levels are within the desired ranges, blood and tissue testing is done every 3 months to monitor the zinc and manganese levels. If the test shows a zinc level of less than 1.0 ppm, additional administrations of chelated zinc in the amount of ½ ounce per administration are performed. If the test shows a manganese level of less than 3.0 ppm, additional administrations of chelated manganese in the amount of ½ ounce per administration are performed. If the results of the blood test show a zinc level of greater than 1.5 ppm, no additional zinc is administered. Instead, blood testing is done on a per parity basis to determine when the zinc level has returned to the optimum range. If the results show a manganese level of greater than 4.0 ppm, no additional manganese is administered. Instead tissue testing is done on a per parity basis to determine when the manganese level has returned to the optimum range.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

I claim:

1. A method of treating farrowing sows to increase pig production, the method comprising the steps of:
   identifying farrowing sows and their offspring;
   determining the zinc concentration of samples taken from the offspring;
   comparing the determined zinc concentration to a predetermined adequate zinc concentration range for swine; and
   modulating the zinc concentration of the offspring by supplying chelated zinc to the farrowing sows when the determined zinc concentration is below the adequate zinc concentration range.

2. The method of claim 1 wherein the samples taken are additionally from the farrowing sows.

3. The method of claim 2 wherein the predetermined adequate zinc concentration ranges from 0.70 ppm to about 1.50 ppm.

4. The method of claim 1 wherein the sample taken is a tissue sample or a blood sample.

5. The method of claim 4 wherein the predetermined adequate zinc concentration ranges from about 40 ppm to about 90 ppm.

6. The method of claim 1 wherein the chelated zinc is supplied in feed made available to the farrowing sows.

7. The method of claim 1 wherein the chelated zinc is supplied in water made available to the farrowing sows.

8. The method of claim 1 wherein the chelated zinc is supplied by injections given to the farrowing sows.

9. The method of claim 1 wherein the chelated zinc is supplied to the farrowing sows while they are lactating.

10. The method of claim 9 wherein the chelated zinc is supplied in feed made available to the farrowing sows.

11. The method of claim 9 wherein the chelated zinc is supplied in water available to the farrowing sows.

12. The method of claim 9 wherein the chelated zinc is supplied by injections given to the farrowing sows.

13. The method of claim 1 further comprising the steps of:
   identifying farrowing sows and their offspring;
   determining the manganese concentration of samples taken from the offspring;
   comparing the determined manganese concentration to a predetermined adequate manganese concentration range for swine; and
   modulating the manganese concentration of the offspring by supplying chelated manganese to the farrowing sows when the determined maganese concentration is below the adequate manganese concentration range.

14. The method of claim 13 wherein the samples taken are additionally from the farrowing sows.

15. The method of claim 14 wherein the predetermined adequate manganese concentration ranges from about 2.3 ppm to about 4.0 ppm.

16. The method of claim 13 wherein the chelated manganese is supplied in feed made available to the farrowing sows.

17. The method of claim 13 wherein the chelated manganese is supplied in water made available to the farrowing sows.

18. The method of claim 13 wherein the chelated manganese is supplied by injections given to the farrowing sows.

19. The method of claim 13 wherein manganese is supplied to the farrowing sows while they are lactating.

* * * * *